United States Patent [19]

Johnson et al.

[11] Patent Number: 4,674,966

[45] Date of Patent: Jun. 23, 1987

[54] APPARATUS FOR FORMING FIBROUS PADS

[75] Inventors: Carl W. Johnson; Kenneth J. Fries, both of Neenah, Wis.

[73] Assignee: Winkler & Dunnebier, Overland Park, Kans.

[21] Appl. No.: 596,002

[22] Filed: Apr. 2, 1984

[51] Int. Cl.$^4$ .............................................. B28B 5/10
[52] U.S. Cl. ..................................... 425/82.1; 19/148
[58] Field of Search ............... 425/80.1, 82.1; 19/148; 264/112, 115, 116, 121, 517, 518; 156/62.2

[56] References Cited

U.S. PATENT DOCUMENTS

| | | | |
|---|---|---|---|
| 2,940,134 | 6/1960 | Heritage | 264/121 |
| 3,201,499 | 8/1965 | Casse | 264/121 |
| 3,846,871 | 11/1974 | Kolbach | 19/148 |
| 4,005,957 | 2/1977 | Savich | 425/80.1 |
| 4,016,628 | 4/1977 | Kolbach | 425/82.1 |
| 4,375,447 | 3/1983 | Chung | 264/121 |

*Primary Examiner*—Peter Chin
*Attorney, Agent, or Firm*—Nicholas A. Kees

[57] ABSTRACT

An apparatus for defiberizing a web of compressed material into fluff and then forming the fluff into pads, and a method of use of the apparatus. The apparatus includes a hammermill or other machine for performing the actual defiberizing. The fluff is then drawn by vacuum which is contained within a shroud, into insert molds which form fluff pads in any shape and contour desired. The insert molds are assembled into a drum which turns continuously such that the vacuum is applied to only certain of the molds. As each mold leaves the shroud, any excess fluff which may overfill the mold is removed and recycled. The pad is then removed from the mold and passed downstream for further processing. The apparatus includes an arrangement for vacuuming out any remaining bits of fiber after the pad is removed. Also included is an apparatus for culling the pads at the discretion of the operator for start-up and shut-down as well as other purposes. The excess fluff which overfills the molds can be removed by scarfing rolls and additionally by air streams which are drawn by the vacuum and directed at the excess fluff as it is removed by the scarfing rolls. The molds themselves are changeable and can be easily replaced if a different shape or size of pad is required, by merely removing the current insert molds and installing ones having the desired shape and contour.

10 Claims, 18 Drawing Figures

APPARATUS FOR FORMING FIBROUS PADS

BACKGROUND OF THE INVENTION

This invention relates to apparatus for forming pads of material from a more compressed form of the same material, and in particular to apparatus for forming the pads in the shape and contour required, including varying the thickness across the width and length of the pads, without the need for later cutting and trimming and the resultant waste.

The conventional method for forming fibrous pads begins by feeding a felted web of compressed material such as wood pulp into a hammermill, where it is defibrated to a light, fluffy material called "fluff". This fluff is then drawn through the screen of the hammermill and onto a screen belt by a source of vacuum below the belt. There is thus formed on the belt a fluff blanket of relatively uniform thickness of about one inch, more or less, across the entire width of the belt, which can be up to 24 inches or more. This blanket of fluff is then conveyed continuously downstream to machines which process it into the particular end products being manufactured, whether they be feminine hygiene pads, disposable diapers, adult incontinence products or other products employing fluff pads.

Conventionally, the processing includes cutting the blanket into the proper shape for the particular product being manufactured, and then wrapping and packaging it for later use. Cutting the blanket into the proper shape, however, can result in a substantial waste of fluff. For instance, to form a product such as a feminine hygiene pad, the blanket must be cut into oval shapes. Generally this is done by use of a rotary die cutter. This creates a "dog-bone" shaped waste between the ends of the respective ovals.

If on the other hand the product is a disposable diaper or adult incontinence product, no waste is created by the cut between the pads, since the edges are straight. The sides, however, are usually cut in the shape of an hourglass to allow space for the legs of the wearer without causing bunching. The cuts required to allow space for the legs again cause waste of fluff.

Moreover, the mere fact that the fluff blanket must be cut at all is a substantial disadvantage. As to the rotary die cutter mentioned above, the tolerances for cutting fluff are extremely close, and so the maintenance costs can be very high. Additionally, any fluff that is cut using a rotary die cutter is left with a very hard edge, since the fluff is very tightly compressed at the edge by such a cutter at the time of cutting. Because such a hard edge would be objectionable for the leg cutouts of disposable diapers and adult incontinence products, due to the skin irritation such a hard edge would cause, water-jet cutting has come to be the conventional method of forming the "hourglass" cuts required, because it results in a fluffy, soft cut edge. Of course water-jet cutting has its own disadvantage, that is, extremely high maintenance costs. These high costs arise from the fact that the water must be forced at extremely high pressure through a fine nozzle:, causing the nozzle to experience high wear rates almost regardless of the material from which the nozzle is made. Further, for the water to be reused in a continuous cutting operation, it must be carefully filtered to avoid clogging the nozzle.

A further disadvantage of the above-described system lies in the screen belt on which the fluff blanket is formed. This screen belt is tautly stretched over the rollers on which it runs. The fact that the screen itself runs on the rollers and is pulled across a vacuum box, which has a perforated top cover, produces friction which causes wear to the screen. As the screen wears, fine bits of metal wire may wear off and may become entangled in the fluff blanket. This situation may give the unsatisfactory result that diapers and feminine hygiene pads may have bits of metal in them, which would cause great irritation or worse.

The entire process of forming a uniform fluff blanket and then cutting fluff pads therefrom has at least one other significant disadvantage: the uniformity of the blanket itself. Thus for instance the absorbent padding of a disposable diaper is the same thickness at the waist portion, which seldom gets wet, as it is between the legs where much moisture must be absorbed, because the thickness of the blanket from which it was cut was uniform throughout its length and width.

Finally, referring to the waste of fluff alluded to above, the raw material used to make this fluff, such as wood pulp, is expensive. Costly machines have been designed and sold simply to recycle, reprocess and reuse this fluff cut out of the shapes described above to avoid discarding this waste and the cost associated therewith.

A patent to Furbeck, U.S. Pat. No. 3,717,905 discloses an apparatus for forming fibrous pads, although that apparatus employs a seal roll as a required component. Two other patents, one to Savich, U.S. Pat. No. 3,939,240 and one to Kolbach, U.S. Pat. No. 3,973,291, disclose methods for forming fibrous pads. Kolbach's method includes a screened belt, which slides over multiple vacuum boxes, with all of the wear problems attendant thereto. Savich's method includes forming larger pads and passing them through smaller openings as a means of forming and compressing the pads. Applicant has discovered that the pads, once formed, do not hold their shape well if later compressed or forced through smaller openings.

This invention relates to solutions to the problems described herein.

SUMMARY OF THE INVENTION

This invention includes a pulp defiberizer, such as a conventional hammermill into which is fed a felted web of compressed, fibrous material, such as wood pulp. The defiberizer grinds the material into a fine, fibrous material called fluff. This fluff is then drawn through a screen in the defiberizer, and deposited onto an interchangeable screen form, called an "insert", by a source of vacuum below the insert. This insert is in the shape of the pad desired, whether that shape be oval for feminine hygiene pads, hourglass for diapers, or any other desired shape. After passing under scarfing rolls, which remove excess fluff, the insert moves to an area where it is shielded from vacuum, and the pad formed therein is removed and the wrapping and packaging of the pad accomplished. Ideally, a group of inserts are assembled in the shape of a wheel so that the process of thus forming the pads can be continuous. In addition to forming the proper outline of the pad, the insert can be constructed so as to form a pad which is thicker in some areas and thinner in others, so that more material is deposited where needed and less where it is not needed.

It is therefore one object of this invention to provide an apparatus for forming fibrous pads in the shape in which they will be used, without the need for later cutting.

Another object of this invention is to provide an apparatus for forming a fibrous pad having varied thickness over its surface.

Yet another object of the invention is to provide an apparatus which vacuum forms fibrous pads by use of interchangeable inserts.

Still another object of this invention is to provide an apparatus employing inserts, for forming fibrous pads, which inserts have a foraminous upper surface, such as a screen, supproted by a foraminous floor which moves along with the screen to minimize wear to the screen.

Other objects and advantages of this invention will become apparent hereinafter.

DESCRIPTION OF THE PREFERRED EMBODIMENTS

Figure 1:
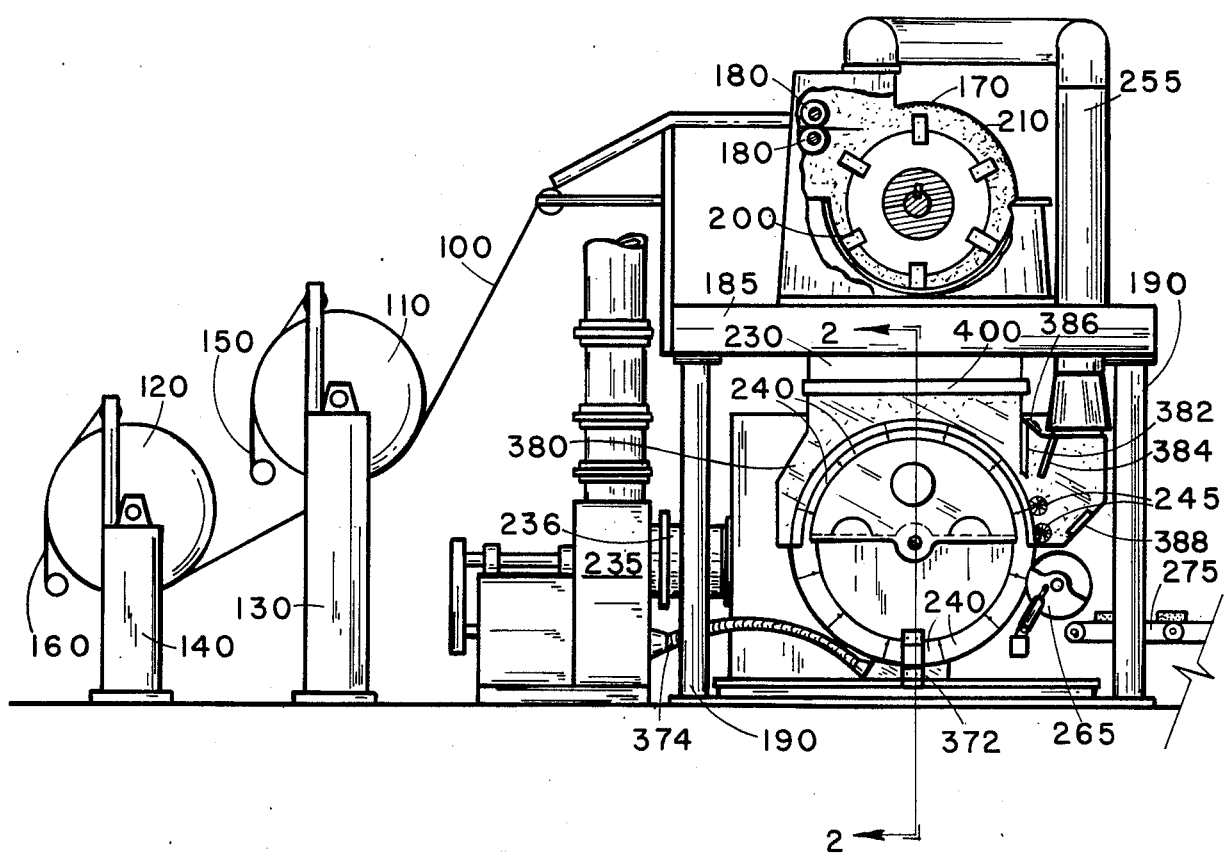
FIG. 1 is an elevation of an apparatus embodying the invention.
Figure 2:
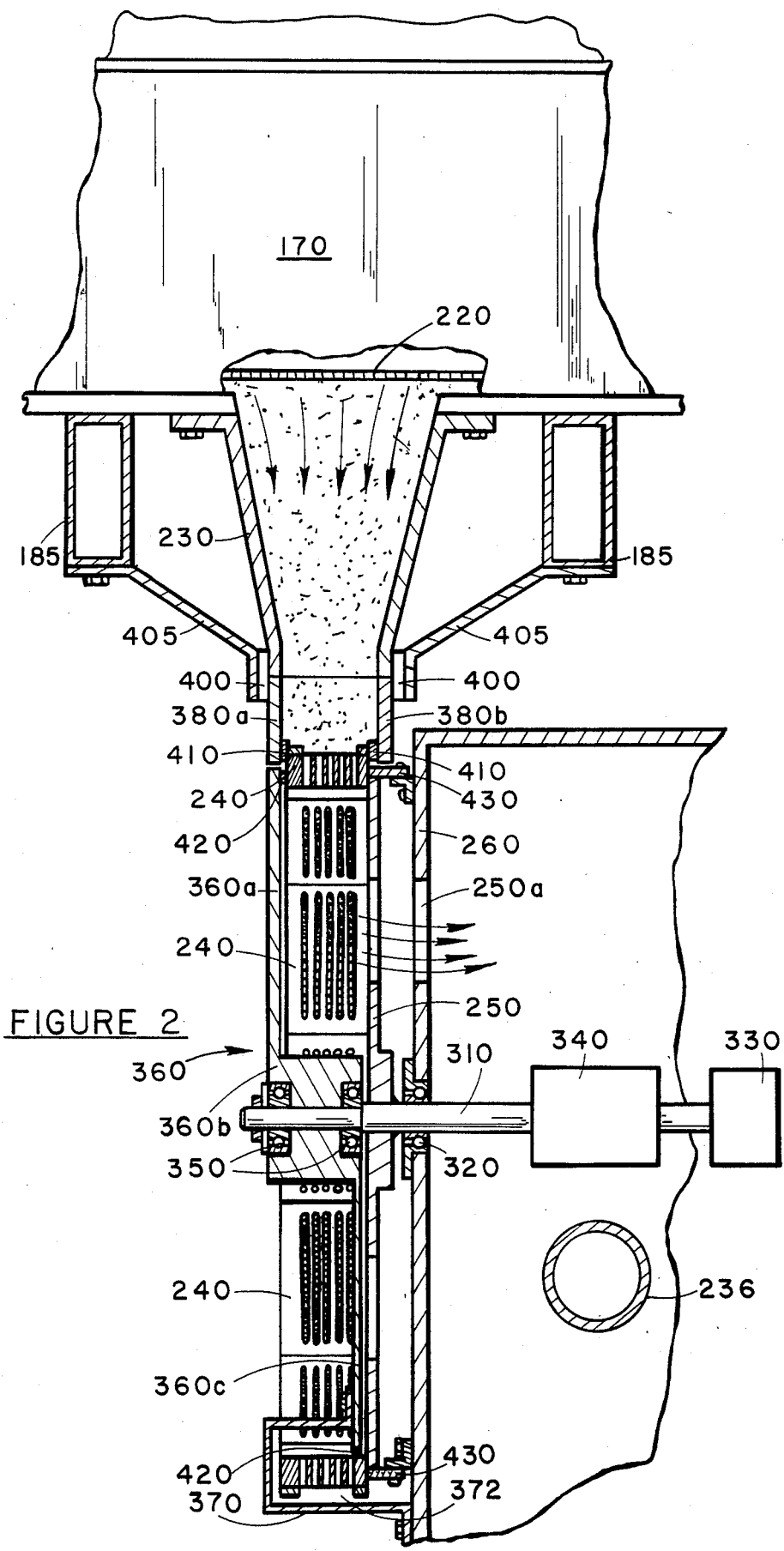
FIG. 2 is a sectional view of FIG. 1 taken along line 2—2.

Very generally, a web of compressed fibrous material 100, shown in FIG. 1, is fed into hammermill 170, fiberized, and the fibers entrained in an air stream caused by vacuum source 235. As shown in FIG. 2, the air stream draws these fibers down onto depressions on the upper surfaces of inserts 240, which are partially foraminous, in the shape and contour of the pad desired. Referring again to FIG. 1, inserts 240 pass under scarfing rolls 245, where the excess fibers are taken off and recycled via stack 255. inserts 240 and the pads therein then pass under takeoff roll 265, where the pads are taken from the inserts and dropped onto a conveyor 275 for wrapping and packaging.

Referring now in more detail to FIG. 1, the embodiment of the invention there shown accepts compressed fibrous material, such as wood pulp, from rolls 110 and 120 on stands 130 and 140, which employ braking devices 150 and 160. While the Figure shows two rolls, meaning that the material is being fed in two thicknesses, the material can be fed in any reasonable number of thicknesses, and can even be fed via sheets as opposed to rolls.

The material 100 is fed into a hammermill 170 between feed rollers 180. Hammermill 170 is generally conventional. Any hammermill generally available which can handle compressed fibrous material, such as the Meteor model from Williams Patent Crusher and Conveyor Company, of St. Louis, would be suitable. In this instance, hammermill 170 rests on crossbeams 185 which in turn are supported by posts 190. The hammers 200 and grinding plate 210 of hammermill 170 work together conventionally to break down the material 100 into its individual fibers, or as nearly thereto as possible, which fibers are then collectively called "fluff". This fluff is drawn through the screen 220 of the hammermill 170 and into a funnel 230 by a vacuum source 235, via a path which can be best explained by reference to FIG. 2.

Referring now to that Figure, the path of the vacuum is from hammermill 170 through its screen 220 and through inserts 240. The vacuum then is turned toward the back of the apparatus (that is, away from the viewer in FIG. 1) and passes through openings 250a in the back of backing plate 250 and openings in the frame 260, behind which the vacuum source 235 (FIG. 1) has its inlet 236 (FIG. 2).

Referring again to the path of the fluff, the vacuum draws the fluff down from the hammermill to be deposited on the foraminous upper surface of insert 240, as can be seen best in FIG. 2, as the vacuum passes through this upper surface and exits the back of the machine as explained above. As shown best in FIGS. 3 and 5, each insert 240 is arcuately shaped and, together with a number of identical inserts 240, form a drum 270. This drum 270 may preferably be located below the hammermill, and its axis may preferably be centered below and parallel to the axis of the hammermill.

Figure 5:
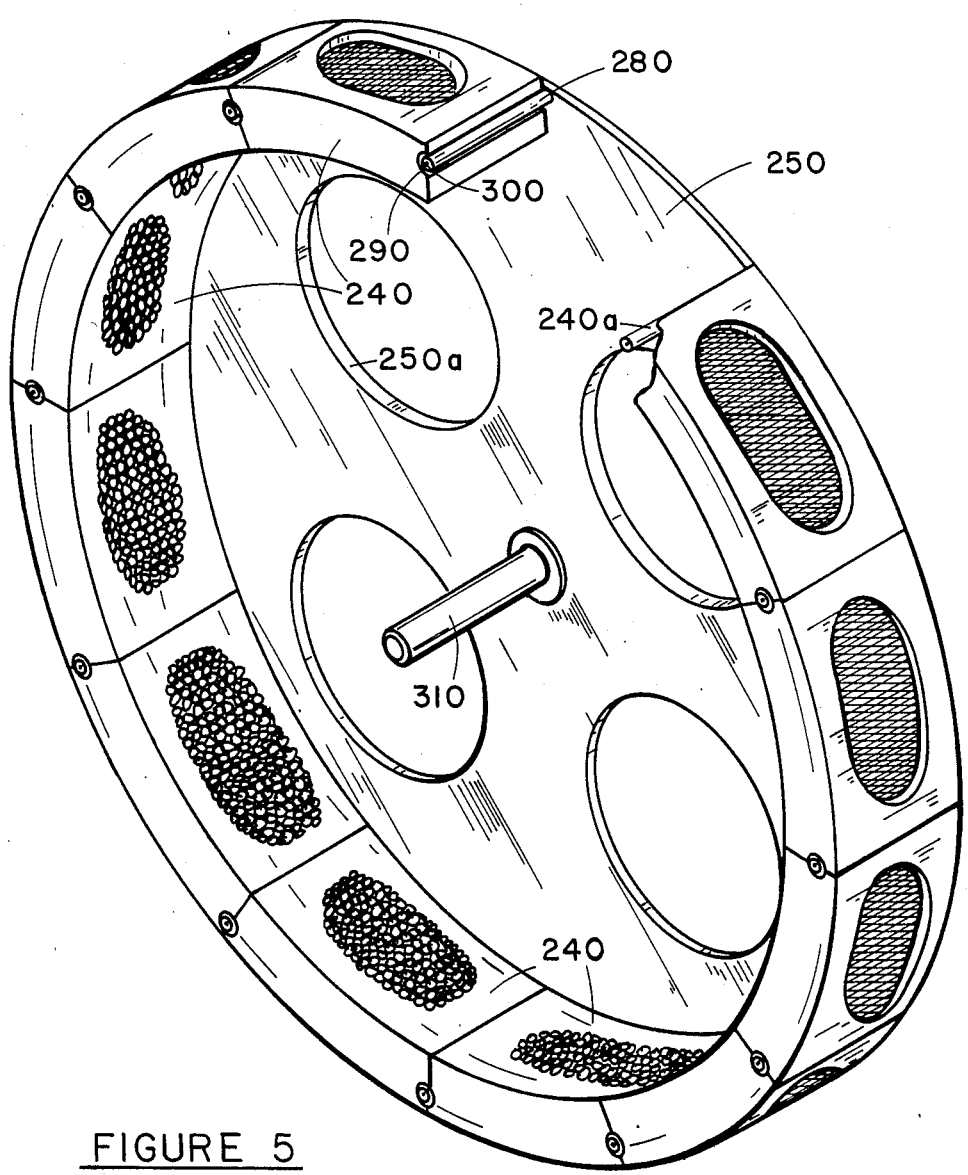
FIG. 5 is an isometric view of a wheel formed by the inserts and backing plate, partially cut away.

As shown in FIG. 5, each insert 240 is removably secured to the edge of backing plate 250 by any suitable means. One preferable means, shown herein, is to thread pegs 280 into plate 250. Inserts 240 can then be formed with a matching semi-cylindrical groove 240a in each end. The spacing of pegs 280 about plate 250 is such that each insert 240 fits tightly between its respective pegs. The length of each peg should be nearly but no greater than the width of the inserts. After each insert is slid between its respective pegs, a bolt 290 and washer 300 are tightened into the outer end of each peg to hold each insert tightly in position. Alternatively the inserts could be simply bolted to plate 250 or affixed in any other secure but removable manner.

Referring again to FIG. 2, plate 250 is fixedly secured to an axle 310, which passes through frame 260 via bearings 320. Axle 310 is then connected to a suitable prime mover 330, such as an electric motor, via a suitable speed reducing arrangement 340, such as reducing gears, or appropriately sized pulleys and belts.

Journaled to axle 310 in front of plate 250, by bearing 350, is a front sealing plate 360 having a rough "S" shape. Front plate 360 includes a semicircular outer portion 360a, a hub portion 360b and a semicircular recessed portion 360c. Hub 360b contains the bearing 350 and is secured to the outer and recessed portions or formed integrally therewith. Outer portion 360a is aligned just outside of the front surface of inserts 240, while recessed portion 360c is aligned just outside of the front surface of plate 250. Finally, connecting portion 360d, shown by broken lines in FIGS. 3 and 4, runs between the outer and recessed portions of the front plate 360 from the hub 360b to the outer edges of the plate. Front plate 360 is prevented from rotating by any suitable means, such as a bracket 370, which is attached to plate 360 and to frame 260.

Finally, a shroud 380, attached to frame 260, surrounds the entire upper portion of the drum 270. The front surface 380a of the shroud 380 is approximately planarly aligned with upper front plate 360a while the rear surface 380b is approximately planarly aligned with plate 250. The purpose of shroud 380 is to provide an area through which the fluff can be dispersed before it is drawn into the inserts, and to close the vacuum path around the inserts.

Figure 3:
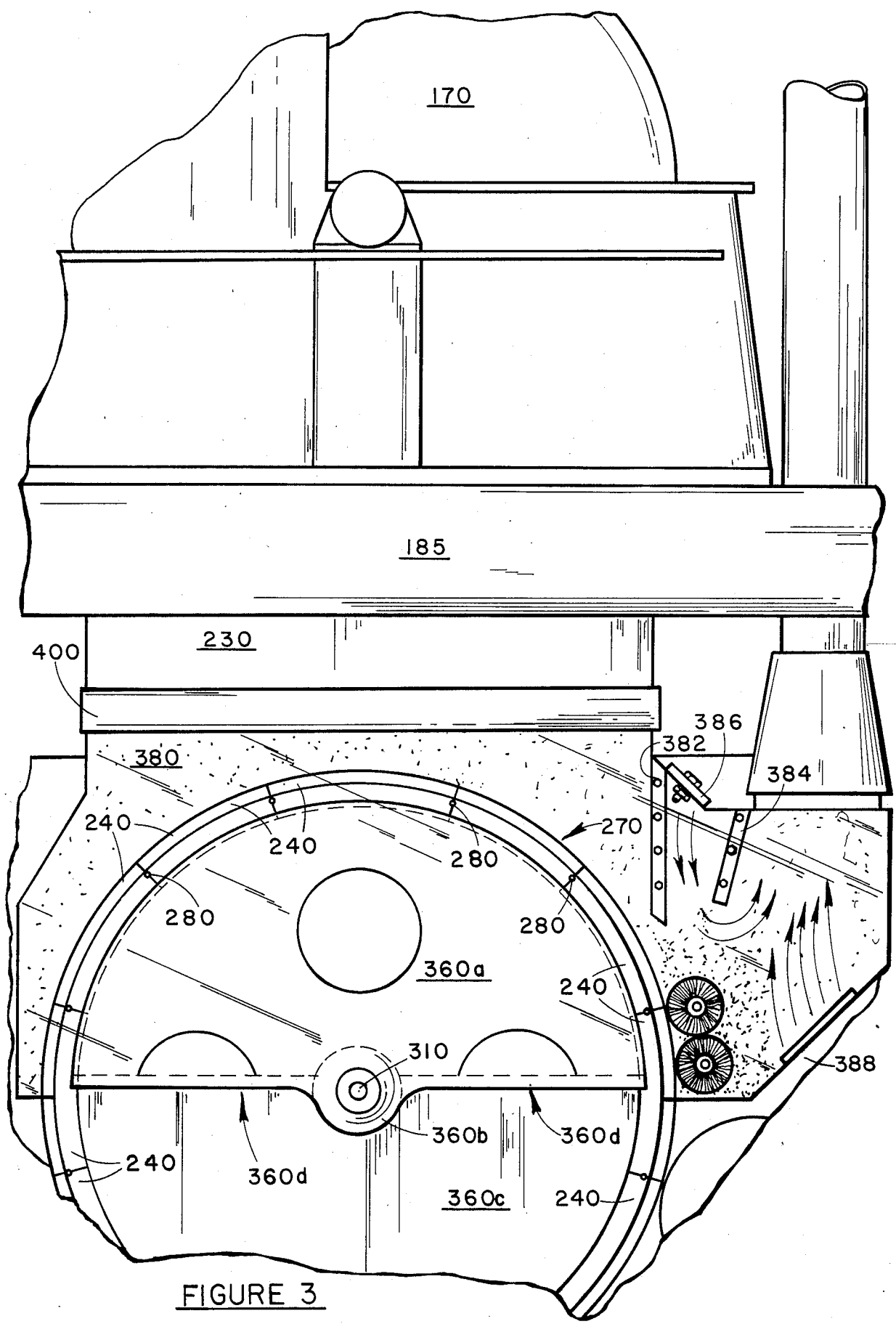
FIG. 3 is an enlarged view of a portion of FIG. 1.
Figure 4:
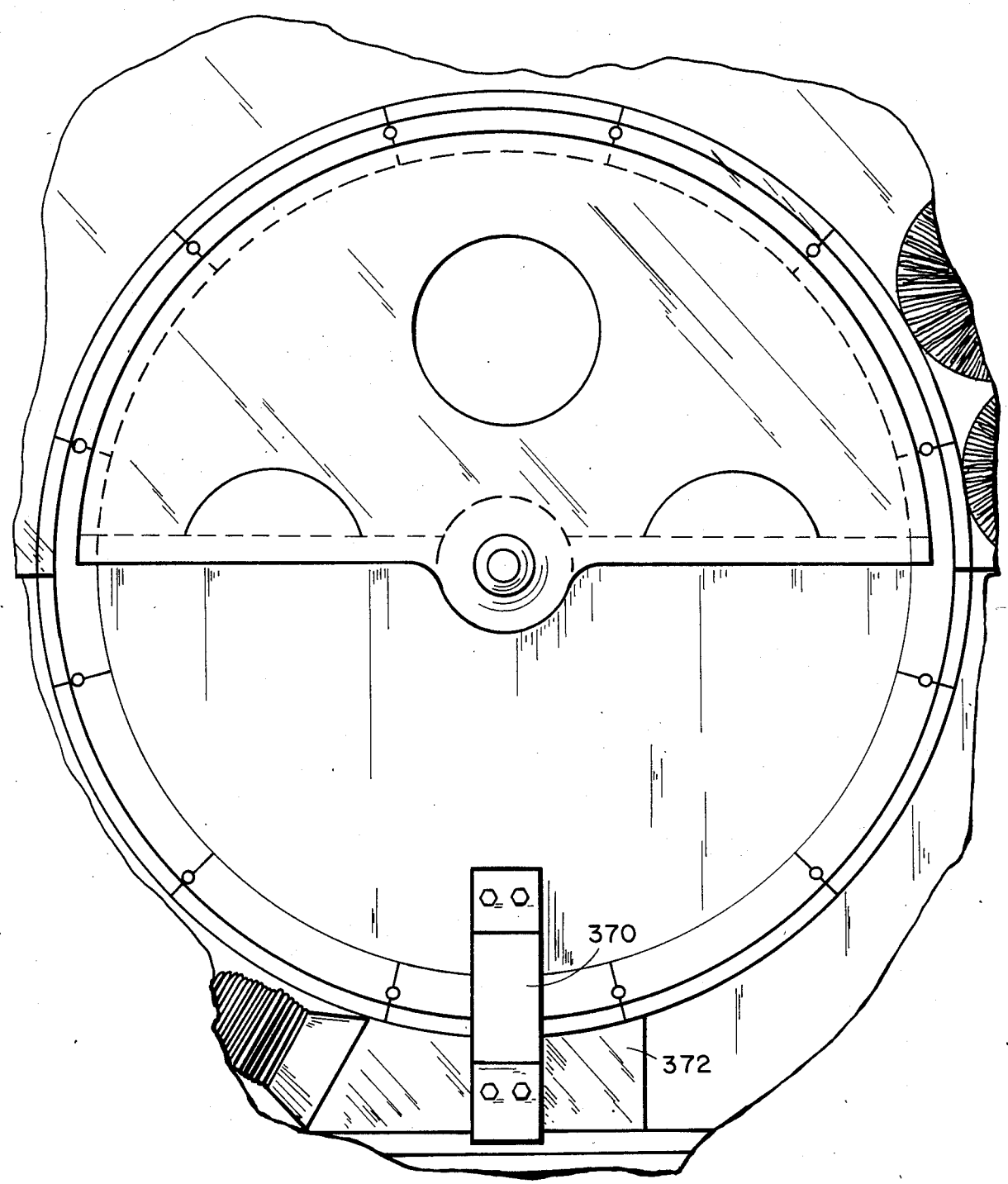
FIG. 4 is a further enlarged view of a portion of FIG. 1.
Figure 16:
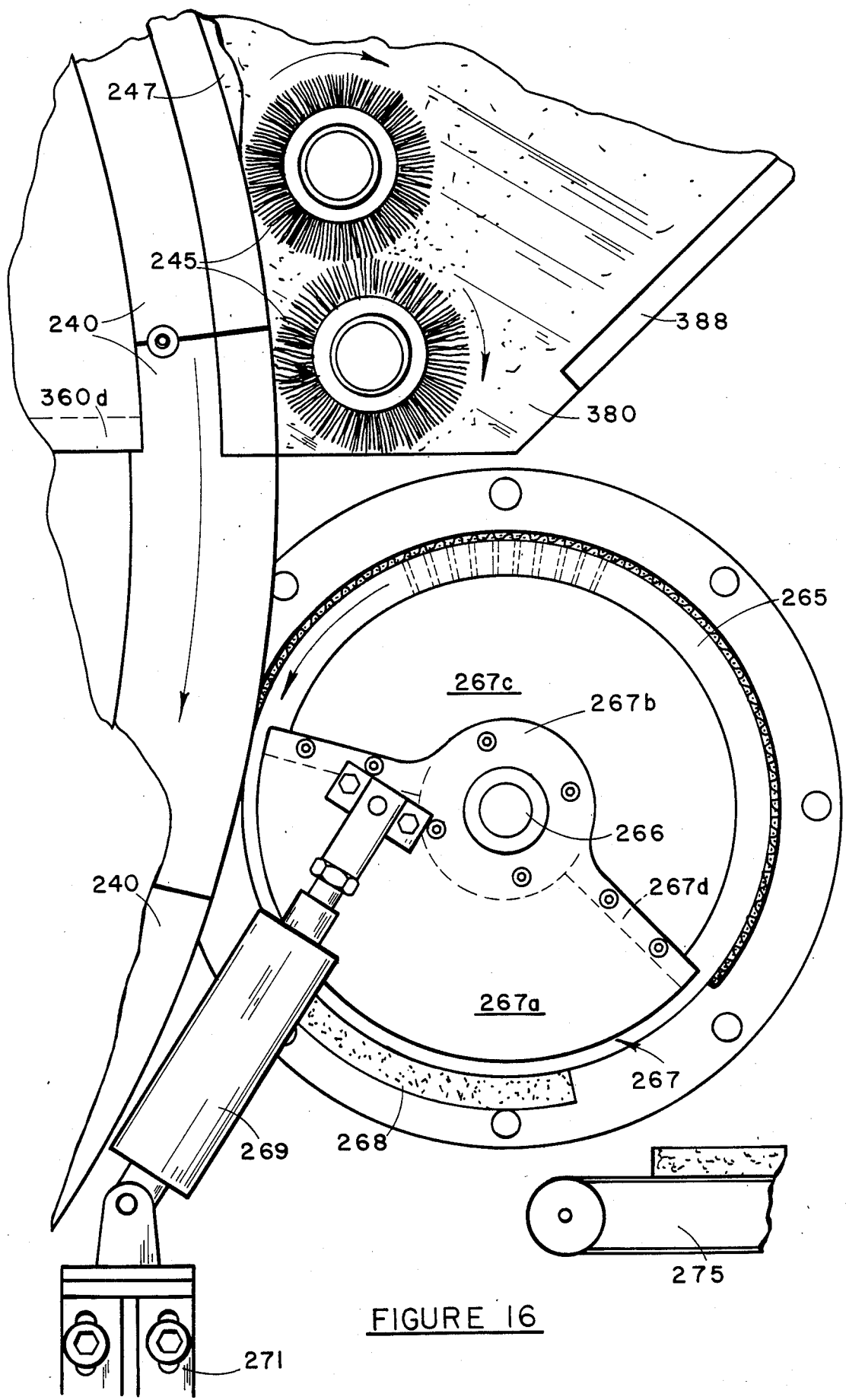
FIG. 16 is an enlarged view of the takeoff roll and scarfing rolls also shown in FIG. 1.

Inserts 240, once filled with fluff, pass under scarfing rolls 245, which can be bristle brush rolls as shown in FIG. 3 or any other type of roll having an abrasive surface. As shown in more detail in FIG. 16, the fluff 247 will normally pile above the upper surfaces of inserts 240. The purpose of scarfing rolls 245, then, is to remove this extra fluff 247 from each pad so that the top of the pad is even with the top surface of insert 240. The scarfing rolls accomplish this function by spinning at high speed in the same direction as drum 270, such that the surface of the roll rubs against the upper surface of inserts 240 and removes the extra fluff therefrom.

To facilitate the recirculation of the loose fluff fibers through stack 255 and hammermill 170 once they are taken off the inserts 240 by scarfing rolls 245, air vanes 382 and 384 and air inlets 386 and 388 are provided inside shroud 380, and are shown best in FIG. 3. In effect, vane 382 separates the area where the fluff pads are formed from the area where the inserts are scarfed and the excess fluff recirculated. As shown by the arrows in FIG. 3, a substantial amount of air enters the apparatus at inlet 388, while a lesser amount enters at inlet 386. Most of the air which composes the airstream carrying the fluff down to inserts 240 comes from inlet 388 originally, and gets to hammermill 170 via stack 255. The purpose of air inlet 386 and vane 384 are to provide a small amount of air flow downward and to the right in FIG. 3 for the purpose of picking up the excess fluff as it is taken off inserts 240 by rolls 245, and carrying the fluff into the air flow caused by inlet 388 for recirculation. Both vanes 382 and 384 reach the entire width of shroud 380, from front surface 380 to rear surface 380b.

As drum 270 continues rotating, it next meets with takeoff roll 265. This takeoff roll has a foraminous surface similar to the surface of the inserts, except that the screening is at the surface rather than recessed. Takeoff roll 265 rotates about its axle 266 at a rate such that the surfaces of it and drum 270 are synchronized. Journaled to axle 266 is a cover plate 267 which is extremely similar to cover plate 360 which covers drum 270, in that cover plate 267 also has an outer portion 267a, a hub 267b, a semi-circular recessed portion 267c and a connecting portion 267d, shown in FIG. 16 in broken lines, which runs between the outer and recessed portions from the hub 267b to the wheel 265. The parts of cover plate 267 can be formed integrally or secured together by bolts or other means.

Similar to cover plate 360, cover plate 267 has vacuum behind the outer portion 267a, which draws air through the part of the takeoff wheel 265 which is behind it. Then, as inserts 240 pass connecting portion 360d of cover plate 360 and move into an area where there is no vacuum behind them, pad 268 is taken out of the insert by takeoff wheel 265 because of the vacuum behind it. The pad 268 then adheres to wheel 265 until it passes to the area where no vacuum is applied, that is, past right connecting portion 267d, and, since the pad is no longer held to takeoff wheel 265, the pad drops onto conveyor 275 to be conveyed to the downstream processing machinery for wrapping and packaging.

Of course, at the start-up or shut-down of an apparatus such as this, certain of the pads may be improperly formed and so a means for culling these pads, that is, keeping them from going onto conveyor 275, is desirable. Hence, cover plate 267 is not fixed in any one position the way cover plate 360 is. Rather, the position of this cover plate is controlled by a cylinder 269, one end of which is pivotably attached to a bracket 267e on cover plate 267 and the other end pivotally attached to a support bracket 271 which is bolted to frame 260. Cylinder 269 may be actuated by air, hydraulics, or any other suitable means. In the position shown in FIG. 16, as described above, the pads 268 drop onto conveyor 275 to be further processed. When cylinder 269 moves to its extended or "cull" position (not shown), however, cover plate 267 rotates clockwise up to 90 degrees. Since the near end of conveyor 275 does not reach as far as the center of wheel 265, the area behind outer portion 267a of cover plate 267 would then not be over conveyor 275, and so the culled pads would drop to the floor below rather than onto conveyor 275. When the pads are again properly formed, cylinder 269 is returned to the position shown in FIG. 16 and pads 268 drop onto conveyor 275 for processing.

As stated above, drum 270 continues to rotate. As it does so, inserts 240 next move away from takeoff roll 265 and toward a cleaning box 372, which is supported in bracket 370. Box 372 applies reverse vacuum to the upper surfaces of inserts 240, which are at that point the bottom surfaces because inserts 240 are upside down at the bottom of drum 270. Box 372 is connected to vacuum source 235 by hosing 374. Hence, any bits of fluff not taken out of inserts 240 by takeoff wheel 265 with pad 268 are cleaned out by vacuum box 372, making the apparatus essentially self-cleaning and selfmaintaining.

Since the entire system is under vacuum it must be sealed, at least to an extent, against the entry of air between the various parts discussed above. The seal need not be complete and total, and in fact it may be advantageous and desirable to have a very small amount of air enter at the various joints between parts. Wholesale entry of air at these points would tend to degrade the level of vacuum, however. Hence, felt or other equivalent seals are provided at various points to keep most of the non-evacuated air out, and are held in place by suitable means. Accordingly, a large seal 400 connects funnel 230 to shroud 380, shown best in FIGS. 2 and 3, and is supported by brackets 405, shown in FIG. 2, which are in turn connected to crossbeams 185. These brackets 405 also provide some support for funnel 230 and shroud 380. Smaller seals 410 close the gaps between shroud 380 and inserts 240 as shown in FIG. 2. Also, seals 420 close the gaps between inserts 240 and front plate 360, while seal 430 reduces air leakage between backing plate 250 and frame 260.

Figure 6:
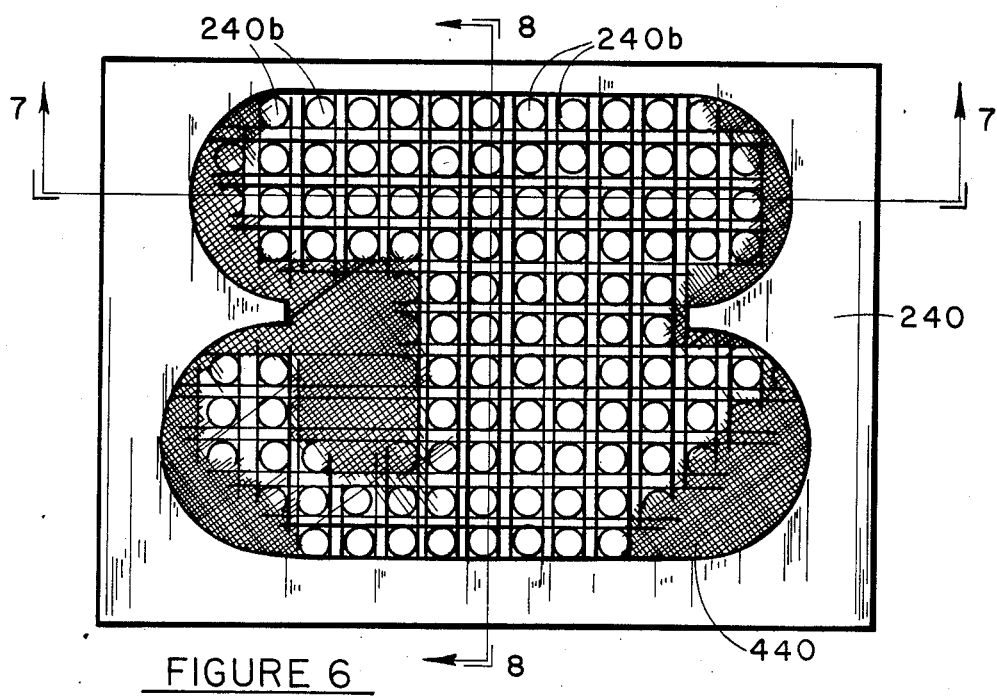
FIG. 6 is a top view of an insert which forms part of one apparatus embodying the invention.
Figure 7:
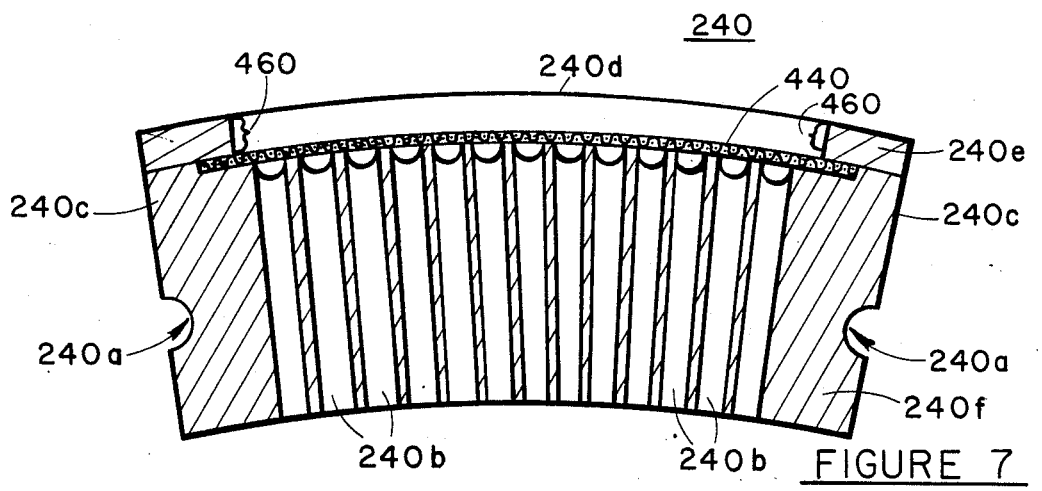
FIG. 7 is a sectional view of FIG. 6 taken along line 7—7.
Figure 8:
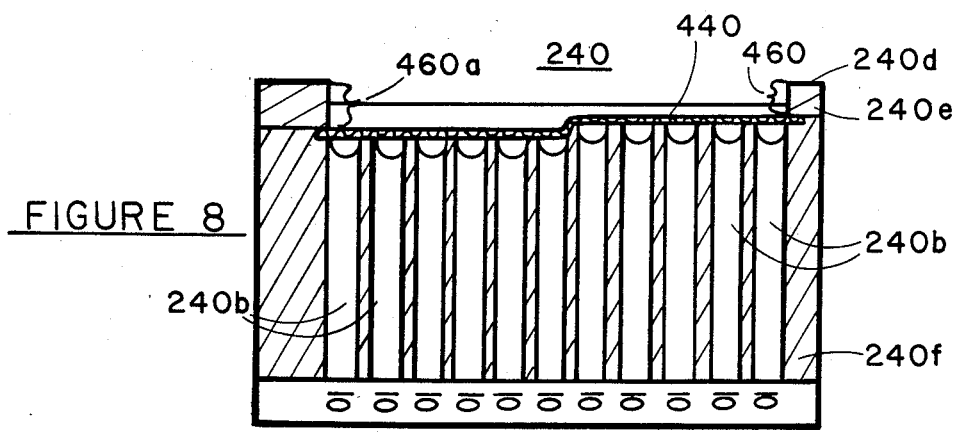
FIG. 8 is a sectional view of FIG. 6 taken along line 8—8.

One of the many possible embodiments of inserts 240 can be seen by reference to FIGS. 6, 7 and 8. The pad to be manufactured using the embodiment shown is of an oval shape although it is formed as a double oval to be folded into a single oval during later processing, possibly after the insertion of super-absorbing material.

A top view of insert 240 is shown in FIG. 6. The necessary foraminous surface is here formed by a screen 440. Screen 440 is partially cut away to show holes 240b beneath, through which the air under vacuum passes.

FIG. 7 is a lengthwise sectional view of the insert 240 shown in FIG. 6. As can be seen in FIG. 7, the contour of insert 240 is an arc of a circle such that a number of inserts 240 can be assembled to form the circumference of a complete drum. Accordingly, holes 240b and sides 240c are formed along lines which radiate from the center of the circle. Screen 440 is set a certain distance 460 below the top surface 240d of insert 240. This distance 460 below surface 240d at which screen 440 is set determines the thickness of the pad being formed. Insert 240 can be molded in a single mold wherein the distance 460 is determined at the time the mold is made. The preferable method, however, is to mold a separate cover 240e and base 240f, place the screen 440 between the two, and permanently adhere them together, such as with epoxy or other suitable adhesive to form insert 240. The upper surface of base 240f then provides a floor for supporting screen 440 without rubbing or wearing the screen itself.

A cross-sectional view of FIG. 6 is shown in FIG. 8. As can be there observed, the way the insert 240 is formed and the way the screen 440 is supported by areas of the base 240f between holes 240b allows the distance between the screen 440 and top surface 240d, and hence the thickness of the pad formed thereby, to vary as necessary. Thus for instance one part of the pad can have thickness 460 while another part can have thickness 460a. Any necessity for cutting or shaping the pad thereafter has been eliminated. Of course, the variance in the thickness of the pad referred to above is determined and set at the time the insert 240 is formed. Once the screen 440 is secured within insert 240, no variance in the distance 460, or in the thickness of the pad formed by insert 240 is possible or even desirable.

Figure 9:
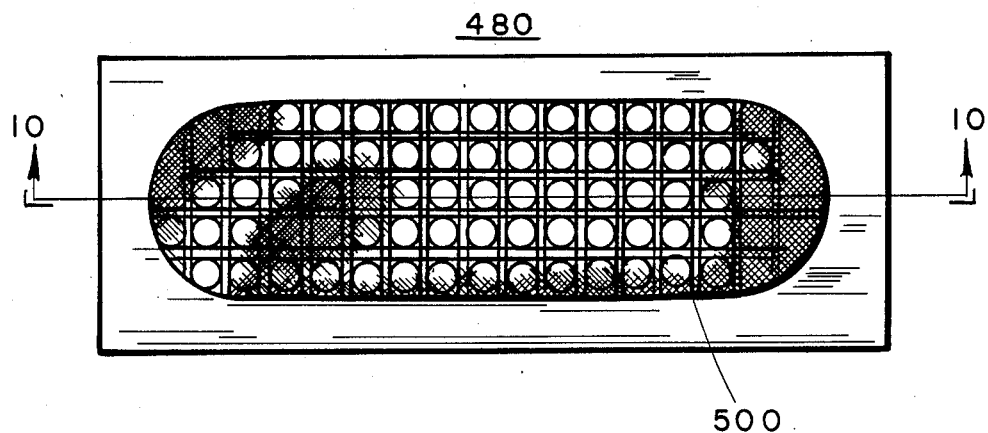
FIG. 9 is a top view of an insert which forms part of another apparatus embodying the invention.
Figure 10:
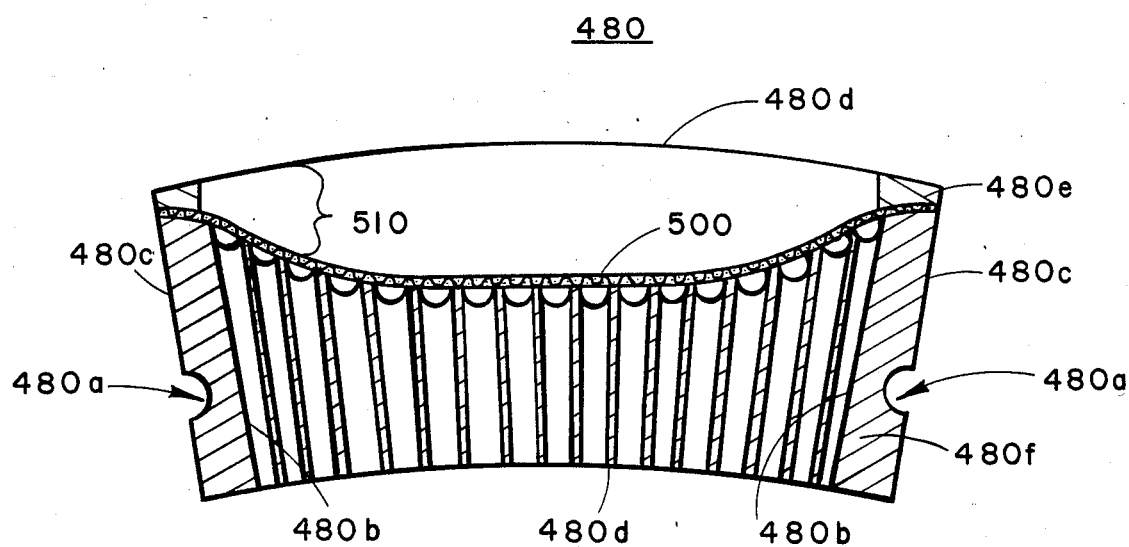
FIG. 10 is a sectional view of FIG. 9 taken along line 10—10.

Another embodiment of an insert to be applied in the instant invention is shown in FIGS. 9 and 10. FIG. 9 is a top view of an insert 480. Insert 480 is used to directly form an oval pad, with no further processing other than wrapping and packaging. As was the case for insert 240, the foraminous surface is here formed by a screen 500. FIG. 10 is a sectional view of insert 480. As can there be seen, screen 500 is again supported within insert 480. Similar to insert 240, insert 480 again is formed having rounded grooves 480a for removably attaching insert 480 to plate 250 by sliding it onto pegs 280. Again, the holes 480b and exterior edges 480c are radial, while the upper and lower edges 480d form an arc of a circle, such that a number of inserts 480 can be assembled to form a complete drum. And again insert 480 can be molded as one part with screen 500 in place, or can be molded as a cover 480e and base 480f and permanently affixed together after 480f provides a floor for supporting screen 500 without rubbing or wearing the screen. Notice that in FIG. 10 the distance 510 from the top surface 480d of insert 480 to screen 500 varies smoothly from a relatively small distance at the ends to a relatively larger distance near the center. This insert 480, then, would form an oval-shaped pad which is thicker near the center than at the edges, without the necessity of any later cutting or folding.

Figure 11:
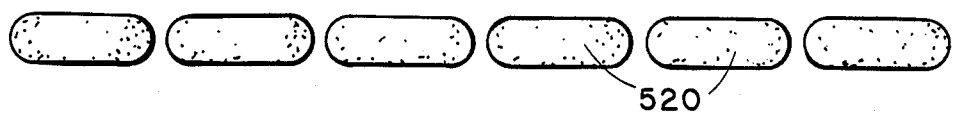
FIGS. 11-15 show a few of the shapes of pads which can be formed by the use of the invention.
Figure 12:
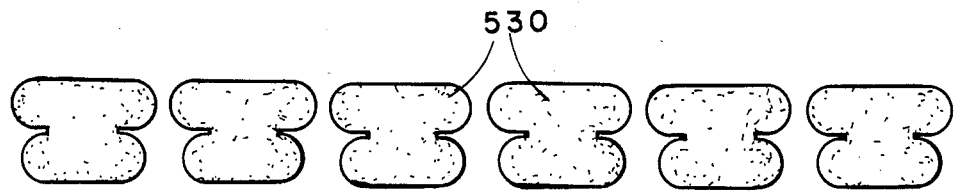
Figure 13:
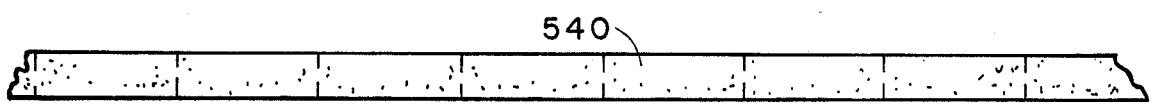
Figure 14:
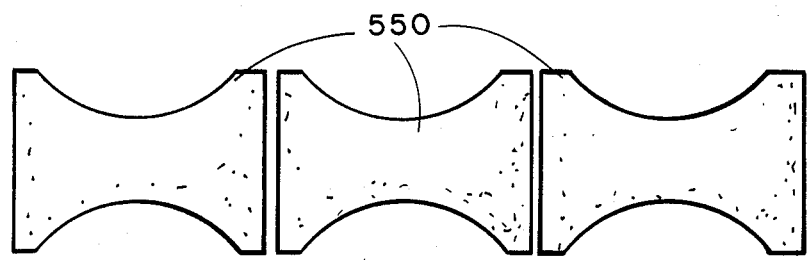
Figure 15:
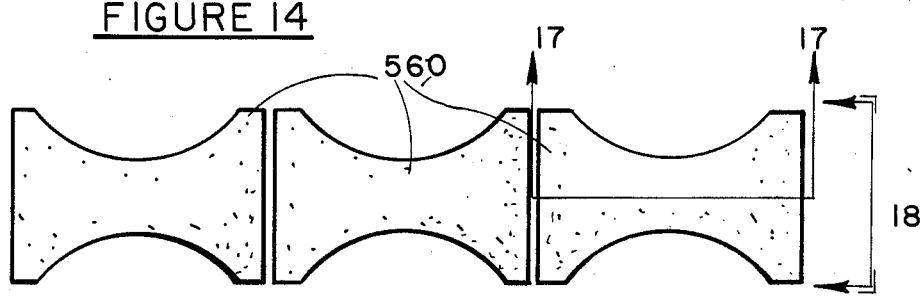
Figure 17:
FIG. 17 is a sectional view of FIG. 15, taken along line 17—17.
Figure 18:
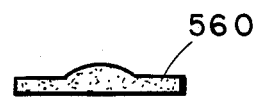
FIG. 18 is a side view of a pad shown in top view in FIG. 15.

This same principle is applied advantageously without regard to the actual shape or contour of the pad to be made. FIG. 11 shows a group of pads 520 formed using insert 480. FIG. 12 similarly shows a group of pads, 530 formed using insert 240. FIG. 13 shows a continuous stream 540 of pad material which could be formed using a group of appropriate inserts. The purpose of an embodiment which forms such a continuous stream of pad material would be to adapt the apparatus disclosed herein to conventional downstream equipment which would cut as well as process and package the individual pads. Shown in FIGS. 14 and 15 are the hourglass-shaped pads 550 and 560, used in making baby diapers and adult incontinence products. Pads 550, shown in FIG. 14, are each formed at a predetermined spacing whereas pads 560, shown in FIG. 15, are formed close together and later separated before wrapping and packaging. Pads 550 and 560 were formed applying the same principle, employing an insert having a screen which was further below the top of the insert in the middle than at the ends. Hence in FIG. 17, which is a longitudinal section of a pad shown in FIG. 15, it can be seen that there is more fluff material in the center of the pad than at the edges. Similarly, in FIG. 18, which is an end view of a pad shown in FIG. 15, it can be clearly seen that the pad 560 is substantially thicker at the center than at the sides.

While the apparatus hereinbefore described is effectively adapted to fulfull the aforesaid objects, it is to be understood that the invention is not intended to be limited to the particular preferred embodiments of pad-forming apparatus herein set forth. Rather, the invention is to be taken as including various equivalents without departing from the scope of the appended claims.

What is claimed is:

1. An apparatus for forming fluff pads, defining the shape thereof in all three dimensions, from a felted web of fibrous material, comprising:

a hammermill having a screened outlet at the bottom thereof, and having an inlet not at the bottom thereof, said hammermill receiving said felted web of fibrous material and converting said fibrous material to fluff, which fluff exits via said screened outlet;

forming drum means for receiving said fluff and using it to form fluff pads, said forming drum means comprising;

a disk-shaped backing plate secured to a shaft;

prime mover means for rotating said shaft and thus said backing plate; and a plurality of pad forming inserts defined by sidewalls having recesses, an air impervious top surface and a foraminous surface recessed below said air impervious top surface such that said top surface surrounds and defines two dimensions of the shape of the pad to be formed, the distance by which the foraminous surface is below the top surface defining the third dimension, said inserts being removably attached to said backing plate by means of pegs secured perpendicularly to said backing plate near the edge of said backing plate, which pegs extend through said recesses in the matching sidewalls of adjoining inserts;

shroud means for providing sealed communication between said hammermill screen and said forming drum means;

a frame having said shaft journaled thereto, and attached to and providing support to said hammermill in spaced relation from said forming drum means;

and vacuum means disposed behind said backing plate, in communication with said inserts, for drawing air in which fluff is suspended out of said hammermill through said screen, through said shroud, through the foraminous surfaces of said inserts and out through openings provided for that purpose in said backing plate, such that the fluff is deposited on the foraminous surfaces of said inserts in the desired three-dimensional shape to form the desired pad.

2. An apparatus as recited in claim 1 wherein said fluff builds up on said foraminous surface to the point of excess, and further comprising scarfing means for removing the excess fluff.

3. An apparatus as recited in claim 2 further comprising a single shroud partially surrounding said drum and said scarfing means, and through which said fluff passes from said hammermill to said foraminous surfaces.

4. An apparatus as recited in claim 3 further comprising sealing means for substantially preventing the entry of air between said shroud and said drum.

5. An apparatus as recited in claim 3 further comprising means for recycling the excess fluff into said hammermill such that the excess fluff is not wasted.

6. An apparatus as recited in claim 5 wherein said recycling means includes air vanes and air inlets so positioned and sized as to carry the excess fluff away from said scarfing means and toward said hammermill so that the excess fluff is recycled and used to make pads.

7. An apparatus as recited in claim 6 wherein said air inlets and air vanes direct air onto the top of said scarfing means so that the excess fluff removed by said scarfing means is recycled.

8. An apparatus as recited in claim 1 further comprising a take-off roll for removing said pads from said inserts, said take-off roll having a conveyor position for conveying the pads onto a conveyor and a culling position for removing the pads but not placing them on a conveyor.

9. An apparatus as recited in claim 1 further comprising vacuum means for cleaning each insert on each rotation of said drum after removal of the pad and before beginning to form a new pad therein.

10. An apparatus as recited in claim 1 wherein said floor supports said foraminous surface only at particular, individual points, such that air is allowed to pass through the majority of said foraminous surface while said foraminous surface retains its shape and thereby produces uniform pads.

* * * * *